_United States Patent_ [19]

Nohara et al.

[11] Patent Number: 4,639,523

[45] Date of Patent: Jan. 27, 1987

[54] AMINOALKYLPHENOXY DERIVATIVES

[75] Inventors: Fujio Nohara, Takaoka; Tomoaki Fujinawa, Toyama, both of Japan

[73] Assignee: Ikeda Mohando Co., Ltd., Toyama, Japan

[21] Appl. No.: 737,489

[22] Filed: May 24, 1985

[30] Foreign Application Priority Data

Jun. 1, 1984 [JP] Japan ................................ 59-112746

[51] Int. Cl.$^4$ .................. C07D 401/12; C07D 417/12; C07D 285/12
[52] U.S. Cl. .................................... 546/209; 546/277; 548/135; 548/141; 540/603
[58] Field of Search ................ 548/135, 141; 546/209, 546/277; 260/245.5

[56] References Cited

U.S. PATENT DOCUMENTS

| | | | |
|---|---|---|---|
| 4,380,638 | 4/1983 | Crenshaw et al. | 548/135 |
| 4,390,701 | 6/1983 | Algieri et al. | 546/235 |
| 4,411,899 | 10/1983 | Baldwin et al. | 548/135 |
| 4,528,375 | 7/1985 | Crenshaw et al. | 548/135 |
| 4,528,377 | 7/1985 | Crenshaw et al. | 548/135 |
| 4,528,378 | 7/1985 | Crenshaw et al. | 548/135 |
| 4,587,254 | 5/1986 | Toyofuku et al. | 548/209 |

FOREIGN PATENT DOCUMENTS

| | | | |
|---|---|---|---|
| 57-165348 | 10/1982 | Japan . | |
| 59-7177 | 1/1984 | Japan . | |
| 59-167586 | 9/1984 | Japan | 548/135 |
| 60-67474 | 4/1985 | Japan . | |

*Primary Examiner*—John M. Ford
*Attorney, Agent, or Firm*—Oblon, Fisher, Spivak, McClelland, & Maier

[57] ABSTRACT

Substituted aminoalkylphenoxy derivatives represented by the general formula of:

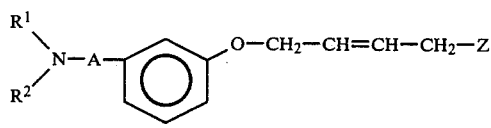

wherein the substituting group Z is either one of the following groups of:

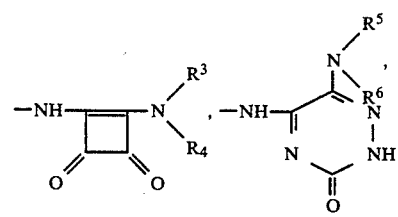

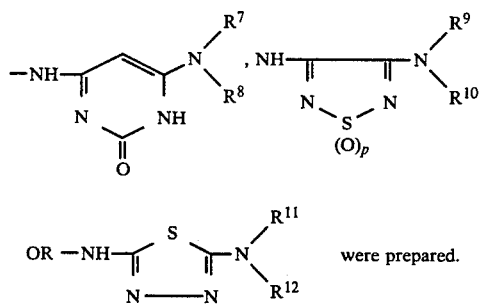

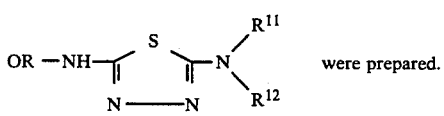

were prepared.

These derivatives exert antagonism against Histamine H$_2$-receptors and hence are efficacious for the treatments of digestive ulcers.

3 Claims, No Drawings

AMINOALKYLPHENOXY DERIVATIVES

BACKGROUND OF THE INVENTION

1. Field of the Invention

The present invention relates to aminoalkylphenoxy derivatives, and more particularly to aminoalkylphenoxy derivatives and medically acceptable salts, hydrates and solvates thereof which exert antagonism to histamine $H_2$-receptors and thus have utility in medical treatment of digestive ulcers.

2. Description of the Prior Art

It has hitherto been well-known in the art that gastric acid secretion can be controlled by blocking the histamine $H_2$-receptors from the histamine action and that gastric secretion in an animal or a human being can be suppressed by the use of a substance having an antagonism to the histamine $H_2$-receptors. (In this connection, reference should be made to R. W. Brimblecombe et al., J. Int. Med. Res., 3, 86, 1975.)

Amongst the known histamine $H_2$-receptor antagonists, particularly well-known is Cimetidine which has been presented in the market as the first commercially available medicine for treating digestive ulcers.

Considerable research has been made to find substances having antagonism to histamine $H_2$-receptors which are superior to that of Cimetidine, and a variety of heterocyclic compounds were synthesized and the antagonism to histamine $H_2$-receptor thereof were investigated. Japanese Patent Laid-Open Publication Nos. 165348/1982 and 7177/1984 will be referred to as pertinent references in this connection, and the contents thereof will be incorporated herein as parts of the specification.

SUMMARY OF THE INVENTION

The object of this invention is to provide novel substituted aminoalkylphenoxy derivatives which exert superior antagonism to histamine $H_2$-receptors to suppress gastric secretion of animals appreciably and which also provide shielding functions to protect the mucous membrane and to promote the secretion of mucus.

The compounds provided by the present invention are aminoalkylphenoxy derivatives represented by the general formula of:

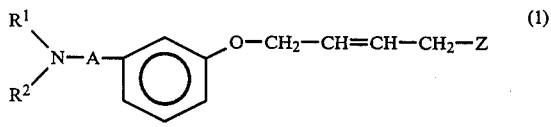

wherein $R^1$ and $R^2$ are individually hydrogen atoms or lower alkyl groups having 1 to 4 carbon atoms, or $R^1$ and $R^2$ form, together with the bonded nitrogen atom, a four to eight member heterocyclic ring which may have a further substiting group or groups; A is a straight-chain or branched-chain alkylene group having 1 to 4 carbon atoms, and Z is either one of the following groups:

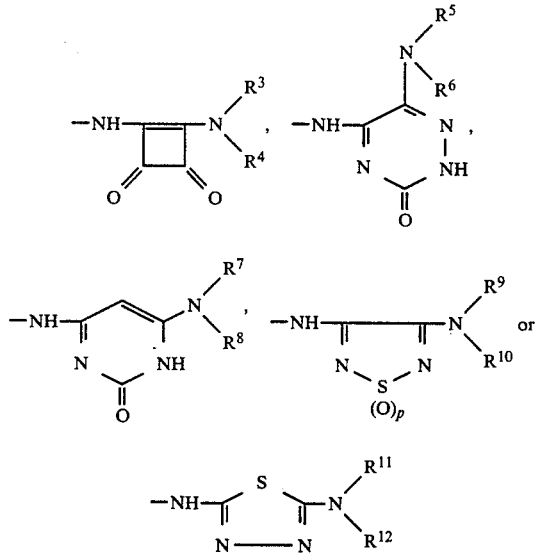

wherein $R^3$, $R^4$, $R^5$, $R^6$, $R^7$, $R^8$, $R^9$, $R^{10}$, $R^{11}$, and $R^{12}$ are individually hydrogen atoms or alkyl, alkenyl, alkynyl, aralkyl or hetrocyclic aryl alkyl groups; or a four to eight member heterocyclic group is formed respectively by $R^3$ and $R^4$, $R^5$ and $R^6$, $R^7$ and $R^8$, $R^9$ and $R^{10}$, $R^{11}$ and $R^{12}$, together with the corresponding nitrogen atoms bonded therewith; and p indicates 0 or 1.

DETAILED DESCRIPTION OF PREFERRED EMBODIMENTS

The present invention will now be described in detail with reference to preferred embodiments thereof.

Initially, examples of the lower alkyl groups having 1 to 4 carbon atoms which are included as either one or both of the groups $R^1$ and $R^2$ are methyl, ethyl, propyl, isopropyl, n-butyl, s-butyl and t-butyl groups.

Examples of the hetrocyclic groups formed by the combination of the groups $R^1$ and $R^2$ together with the nitrogen atom bonded therewith are azetidino-, pyrrolidino-, piperidino- and perhydroazepino- groups. These heterocyclic rings may include further substituent groups, such as hydroxyl, methoxy, ethoxy and lower alkyl groups having 1 to 6 carbon atoms.

Examples of alkylene groups, identified by A, include methylene, ethylene, propylene and isobutylene.

In the group Z contained in the general formula defined in the claim, the groups $R^3$ to $R^{12}$ include, for example, alkyl groups having 1 to 4 carbon atoms, such as methyl, ethyl, n-propyl, iso-propyl, n-butyl, sec-butyl and t-butyl; alkenyl groups, such as ethynyl, 2-propynyl, 2-butenyl and 3-butenyl; alkynyl groups, such as 2-propargyl; aralkyl groups, such as benzyl; and heterocyclic aryl alkyl groups, such as 2-pyridinomethyl, 3-pyridinomethyl, 2-thiophenomethyl, 3thiophenmethyl, 2-furanomethyl and 3-furanomethyl.

Preferred heterocyclic groups, which are formed, respectively, by $R^3$ and $R^4$, $R^5$ and $R^6$, $R^7$ and $R^8$, $R^9$ and $R^{10}$, $R^{11}$ and $R^{12}$, together with the corresponding nitrogen atoms bonded therewith, are azetidino-, pyrrolidino- and piperidino-rings.

The compounds of the invention represented by the general formula (1) may be either in the cis or trans geometrical isomer forms.

Illustrative examples of the compounds provided by the invention and represented by the general formula (1) are the following compounds including those specifically referred to in the Examples given hereinafter.

1-amino-2-[4-<3-(1-pyrrolidino-methyl)phenoxy>-cis-2-butenylamino]-1-cyclobuten-3,4-dione;

1-methylamino-2-[4-<3-(1-pyrrolidino-methyl)phenoxy>-cis-2-butenylamino]-1-cyclobuten-3,4-dione;

1-(2-n-propylamino)-2-[4-<3-(1-pyrrolidino-methyl)phenoxy>-cis-2-butenylamino]-1-cyclobuten-3,4-dione;

1-amino-2-[4-<3-(dimethylaminomethyl)phenoxy>-cis-2-butenylamino]-1-cyclobuten-3,4dione;

1-amino-2-[4-<3-(1-piperidinomethyl)phenoxy>-trans-2-butenylamino]-1-cyclobuten-3,4-dione;

1-methylamino-2-[4-<3-(1-piperidinomethyl)phenoxy>-trans-2-butenylamino]-1-cyclobuten-3,4-dione;

1-amino-2-[4-<3-[1-(1-piperidino)ethyl]phenoxy>-cis-2-butenylamino]-1-cyclobuten-3,4-dione;

1-methylamino-2-[4-<3-[1-(1-piperidino)ethyl]phenoxy>-cis-2-butenylamino-1-cyclobuten-3,4-dione;

1-amino-2-[4-<3-(3-hydroxy-1-piperidinylmethyl)phenoxy>-cis-2-butenylamino]-1-cyclobuten-3,4-dione;

1-methylamino-2-[4-<3-(1-perhydroazepinylmethy)phenoxy>-cis-2-butenylamino]-1-cyclobuten-3,4-dione;

1-benzylamino-2-[4-<3-(1-piperidinomethyl)phenoxy>-cis-2-butenylamino]-1-cyclobuten-3,4-dione;

1-(2-pyridylmethylamino)-2-[4-<3-(1-piperidinomthyl)phenoxy>-cis-2-butenylamino]-1-cyclobuten-3,4-dione;

1-(3-pyridylmethylamino)-2-[4-<3-(1-piperidinomethyl)phenoxy>-cis-2-butenylamino]-1cyclobuten-3,4-dione;

1-(2-thiophenomethylamino)-2-[4-<3-(1-piperidinomethyl)phenoxy>-cis-2-butenylamino]-1-cyclobuten-3,4-dione;

1-(3-thiophenomethylamino)-2-[4-<3-(1-piperidinomethy)phenoxy>-cis-2-butenylamino]-1-cyclobuten-3,4-dione;

6-amino-5-[4-<3-(1-piperidinomethyl)phenoxy>-trans-2-butenylamino]-1,2,4-triazin-3-one;

6-methylamino-5-[4-<3-(1-piperidinomethyl)phenoxy>-trans-2-butenylamino]-1,2,4-triazin-3-one;

6-amino-5-[4-<3-(1-pyrrolidinomethyl)phenoxy>-cis-2-butenylamino]-1,2,4-triazin-3one;

6-methylamino-5-[4-<3-(1-pyrrolidinomethyl)phenoxy>-cis-2-butenylamino]-1,2,4-triazin-3one;

6-ethylamino-5-[4-<3-(1-pyrrolidinomethyl)phenoxy>-cis-2-butenylamino]-1,2,4-triazin-3-one;

6amino-5-[4-<3-(3-hydroxy-1-piperidinomethyl)phenoxy>-cis-2-butenylamino]-1,2,4-triazin-3-one;

6-methylamino-5-[4-(3-dimethylaminomethylphenoxy)-cis-2-butenylamino>-1,2,4-triazin-3-one; 6-methylamino-5-[4-(3-dimethylaminomethylphenoxy)-trans-2-butenylamino]-1,2,4-triazin-3-one;

6-amino-5-[4-<3-(1-perhydroazepinylmethyl)phenoxy>-cis-2-butenylamine]-1,2,4-triazin-3-one;

6-methylamino-5-[4-<3-(1-perhydroazephnylmethyl)phenoxy>-cis-2-butenylamino]-1,2,4-triazin-3-one;

4-amino-6-[4-<3-(1-piperidinomethyl)phenoxy>-trans-2-butenylamino]-(1H)-pyrimidin-2-one;

4-methylamino-6-[4-<3-(1-piperidinomethyl)phenoxy>-cis-2-butenylamino]-(1H)-pyrimidin-2-one;

3-[4-<3-(1-piperidinomethyl)phenoxy>-trans-2-butenylamino]-4-amino-1,2,5-thiadiazol;

3-84-<3-(1-piperidinomethyl)phenoxy>-trans-2-butenylamino]-4-methylamino-1,2,5-thiadiazol;

3-[4-<3-(1-piyrrolidinomethyl)phenoxy>-cis-2-butenylamino]-4-amino-1,2,5-thiadiazol;

3-[4-<3-(1-pirrolidinomethyl)phenoxy>-cis-2-butenylamino]-4-methylamino-1,2,5-thiadiazol;

3-[4-<3-(dimethylaminomethyl)phenoxy>-cis-2-butenylamino]-4-methylamino-1,2,5-thiadiazol;

3-[4-<3-(1-piperidinomethyl)phenoxy>-trans-2-butenylamino]-4-amino-1,2,5-thiadiazol-1-oxide;

3-[4-<3-(1-piperidinomethyl)phenoxy>-trans-2-butenylamino]-4-methylamino-1,2,5-thiadiazol-1-oxide;

3-[4-<3-(1-piperidinomethyl)phenoxy>-trans-2-butenylamino]-4-propargylamino-1,2,5-thiadiazol-1-oxide;

3-[4-<3-(1pirrolidinomethyl)phenoxy>-cis-2-butenylamino]-4-methylamino-1,2,5-thiadiazol-1-oxide;

3-[4-<3-(dimethylaminomethyl)phenoxy>-cis-2-butenylamino]-4-methylamino-1,2,5-thiadiazol-1-oxide;

3-[4-<3-(1-piperidinomethyl)phenoxy>-cis-2-butenylamino]-4-benzylamino-1,2,5-thiadiazol-1-oxide;

3-[4-<3-(1-piperidinomethyl)phenoxy>-cis-2-butenylamino]-4-(2-pyridinomethylamino)-1,2,5-thiadiazol-1-oxide;

3-[4-<3-1(1-piperidinomethyl)phenoxy>-cis-2-butenylamino]-4-(3-pyridinomethylamino)-1,2,5-thiadiazol-1-oxide;

3-[4-<3-(1-piperidinomethyl)phenoxy>-cis-2-butenylamino]-4-(2-thiophenomethylamino)-1,2,5-thiadiazol-1-oxide;

3-[4-<3-(1-piperidinomethyl)phenoxy>-cis-2-butenylamino]-4-(3-thiophenomethylamino)-1,2,5-thiadiazol-1-oxide;

2[4-<3-(1-piperidinomethyl)phenoxy>-cis-2-butenylamino]-5-amino-1,3,4-thiadiazol;

2-[4-<3-(1-piperidinomethyl)phenoxy>-cis-2-butenylamino]-5-methylamino-1,3,4-thiadiazol;

2-[4-<3-(1-pyrrolidinomethyl)phenoxy>-cis-2-butenylamino]-5-amino-1,3,4-thiadiazol;

2-[4-<3-(1-pyrrolidinomethyl)phenoxy>-cis-2-butenylamino]-5-methylamino-1,3,4-thiadiazol;

2-[4-<3-(dimethylaminomethyl)phenoxy>-cis-2-butenylamino]-5-amino-1,3,4-thiadiazol;

2-[4-<3-(dimethylaminomethyl)phenoxy>-cis-2-butenylamino]-5-methylamino-1,3,4-thiadiazol;

2-[4-<3-(1-piperidinomethyl)phenoxy>-trans-2-butenylamino]-5-amino-1,3,4-thiadiazol;

2-[4-<3-(1-pyieridinomethyl)phenoxy>-trans-2-butenylamino]-5-methylamino-1,3,4-thiadiazol;

2-[4-<3-(1-pyrrolidinomethyl)phenoxy>-trans-2-butenylamino]-5-ethylamino-1,3,4-thiadiazol; and 2-[4-<3-(1-pyrrolidinomethyl)phenoxy>-trans-2-butenylamino]-5-n-propylamino-1,3,4-thiadiazol.

The compounds of the invention represented by the general formula (1) and the salts thereof may be prepared, depending on the substituents Z included therein, through the following different processes.

(A) Compounds wherein Z is

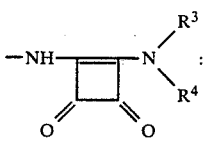

First Step:

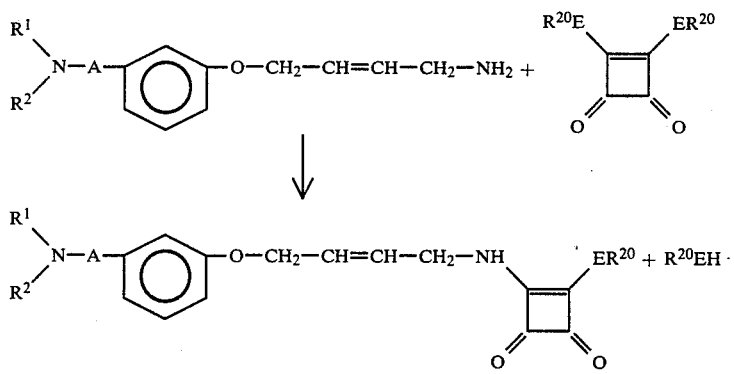

Second Step:

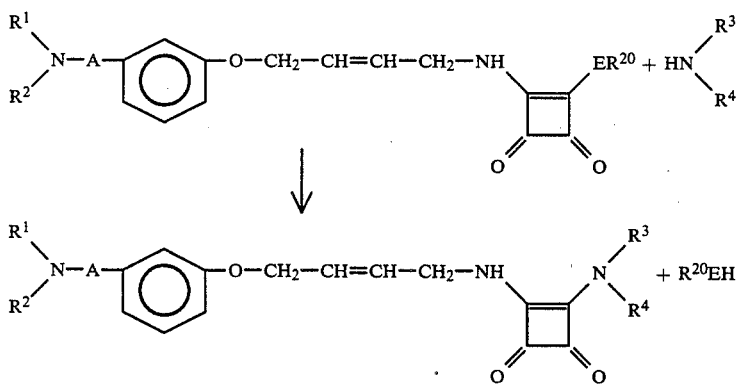

In the reaction equations set forth above, $R^1$, $R^2$, $R^3$ and $R^4$ are the groups as described hereinbefore and defined in the claims; $R^{20}$ is a lower alkyl, preferably methyl; and E is —O— or —S—, preferably —O—.

The first and second steps may be carried out separately, but it is preferable that both stpes be carried out as continuous sequence. It is preferred that both of the starting materials are used in the equivalent molar ratio in the first step, whereas in the second step it is preferred that the amine

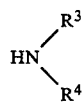

is used in an excess amount, for example, in an amount of two to five times the moles of the resultant produact of the first step.

Both steps may be carried out without using a solvent or may be carried out in a solvent, and an inert organic solvent, such as methanol, ethanol, propanol, acetonitrile or chloroform, may be used in the latter case. The reaction temperature ranges generally from 0° C. to the boiling point of the used solvent, the boiling points of the usable solvents ranging generally from 50° C. to 150° C., and the preferable temperature range is from room temperature to 80° C. The time required for the completion of reaction is varied depending on the reaction temperature, and both reactions may be completed within 30 minutes to 24 hours.

The following known compounds may be used as the exemplary starting materials in the first step.

For instance, the compounds represented by the formula:

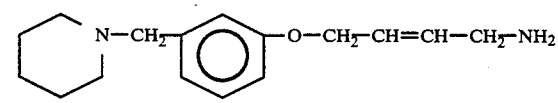

may be prepared by the process disclosed in the specification of Japanese Patent Laid-Open Publication No. 165348/1982; and the derivatives thereof may be prepared through similar processes.

On the other hand, one of the compounds represented by the formula:

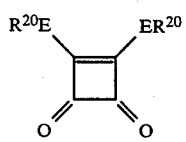

i.e. the compound

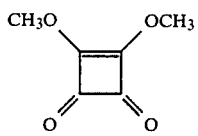

may be prepared by the process disclosed by Sidney Cohenet et al, in J. Am. Chem. Soc., 88 (7), 1533 (1966).

(B) Compounds wherein Z is

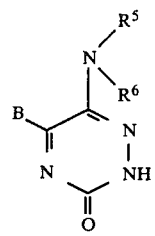

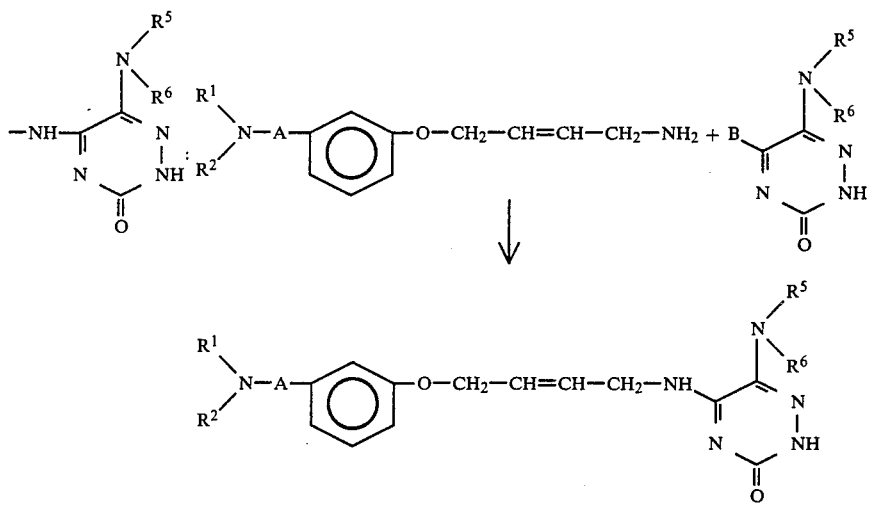

wherein $R^1$, $R^2$, $R^5$, $R^6$ and A are the same as defined above; and B is $R^{30}S$— ($R^{30}$ being an alkyl group, preferably methyl) or a halogen (chlorine, bromine or iodine) atom.

The reaction set forth above may proceed at 50° C. to 150° C. in an inert organic solvent or without using any solvent. Examples of the inert solvents include alcohols, preferably methanol, ethanol and propanol, and the reaction may proceed preferably under reflux of such a solvent.

The compounds represented by the formula:

may be prepared by the process reported by C. C. Tzeng et al, in J. Org. Chem., 26, 1118 (1961), or by a modified process thereof which should be obvious to those having ordinary skill in the art.

(C) Compounds wherein Z is

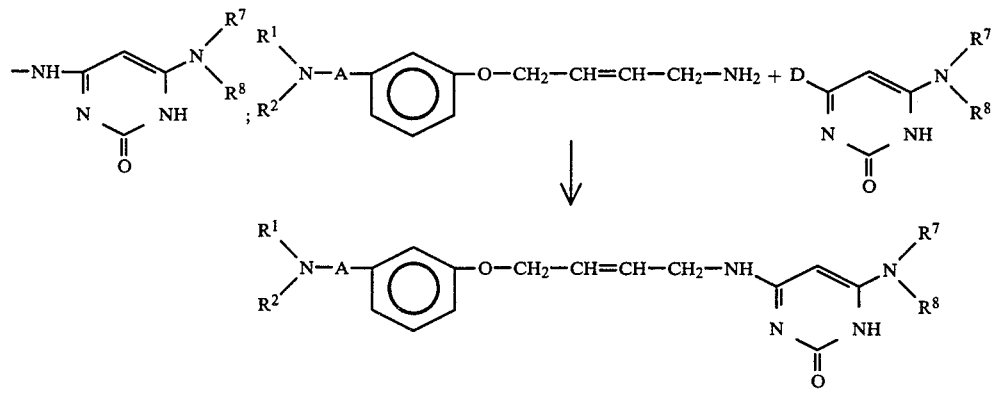

wherein $R^1$, $R^2$, $R^7$ and $R^8$ are the same as defined above; and D is a halogen (chlorine, bromine and iodine) atom or a lower alkylthio group.

The compounds represented by the following formula:

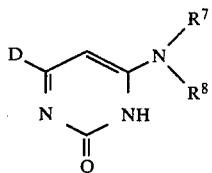

for example hydrochloride of 6-amino-4-chloro-2(1H)-pyrimidone, may be prepared by the process reported by Wolfgang Pfleiderane et al, in Ann., 657, 149 (1962). The reaction may proceed in a solvent or without using any solvent. Usable solvents include, for example, methanol, ethanol, water, DMF and DMSO. The reaction may proceed at 50° C. to 150° C. for 5 minutes to 24 hours under agitation.

(D) Compounds wherein Z is

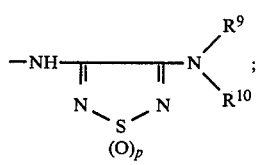

First Step:

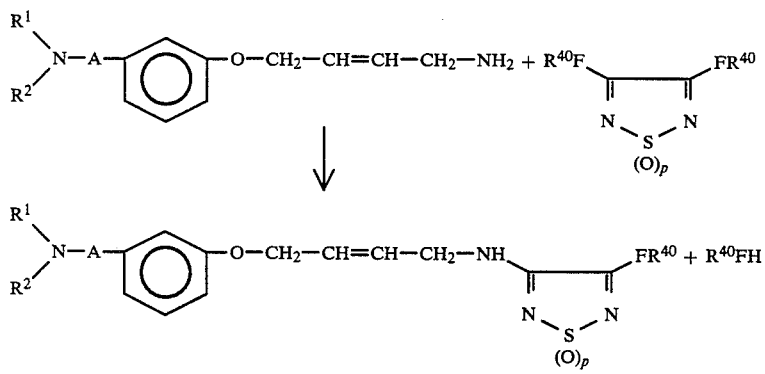

Second Step:

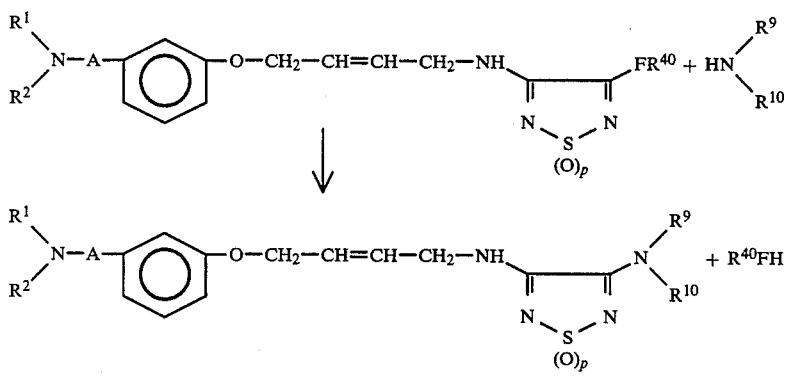

wherein $R^1$, $R^2$, $R^9$, $R^{10}$ and p are the same as defined above; $R^{40}$ is a lower alkyl, preferably methyl; and F indicates —S— or —O—.

The compounds used in the first step and represented by the formula:

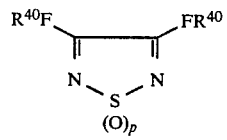

are known compounds, and 3,4-dimethoxy-1,2,5-thiaziazol

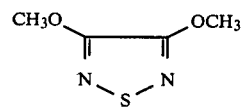

(p=0) may be prepared by a process reported by A. P. Komin et al. in J. Org. Chem., 40, 2749 (1975) or a modified process thereof and 3,4-dimethoxy-1,2,5-thiaziazol-1-oxide

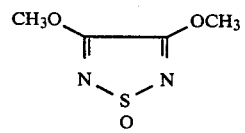

(p=1) may be prepared by a process described in Japanese Patent Laid-Open Publication No. 40675/1981 or by a modified process thereof.

The first step set forth hereinabove may be carried out, for example, by reacting one mole of a derivative of 4-<(3-dialkylaminoalkyl)phenoxymethyl>-2-butenylamine with one to three moles of 3,4-dimethoxy-1,2,5-thiadiazol or 3,4-dimethoxy-1,2,5-thiadiazol-1- oxide in the absence of a solvent or in an inert organic solvent (a lower alcohol, preferably methanol, ethanol or propanol) at a reaction temperature of from −10° C. to 100° C., preferably from 0° C. to 30° C. under agitation. The reaction is completed within 30 minutes to 24 hours, and the end of the reaction may be checked by means of T.L.C. thin layer chromatography.

The reaction of the first step may be continued to the reaction of the second step in a continuous operation sequence. Alternatively, the second step operation may be carried out after refining the resultant product of the first step, for example, by means of column chromatography.

The second step operation is carried out by dissolving the resultant product of the first step in an inert organic solvent followed by addition of an amine compound represented by the formula of:

2 to 10 moles of amine, relative to one mole of the resultant produce of the first step, are used; and the second step is carried out generally at a reaction temperature of from −10° C. to 100° C., preferably from 0° C. to 30° C. The reaction is completed within 30 minutes to 12 hours. When $R^9$ and $R^{10}$ are bydrogen atoms, the resultant product of the second step, for instance, 3-[4-(3-dialkylaminoalkylphenoxy)-2-butenylamino]-4-amino-1,2,5-thiadiazol-1-oxide:

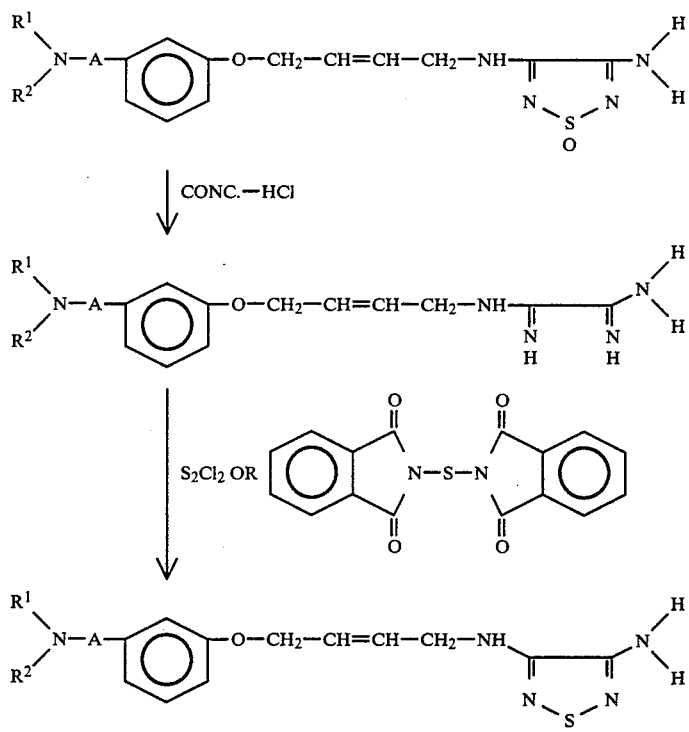

may be treated with a mineral acid to obtain N-[4-(3-dialkylaminoalkylphenoxy)-2-butenyl]ethanediimidamide or a mineral acid salt thereof. Thereafter, the resultant product may be reacted with 1 to 10 moles of sulfur monochloride or N,N'-thiobisphthalimide, relative to one mole of the resultant product to convert into 3-[4-(3-dialkyl-aminoalkylphenoxy)-2-butenylamino]-4-amino-1,2,5-thiadiazol.

Other than the aforementioned process, the same product can be prepared through the following sequential reactions:

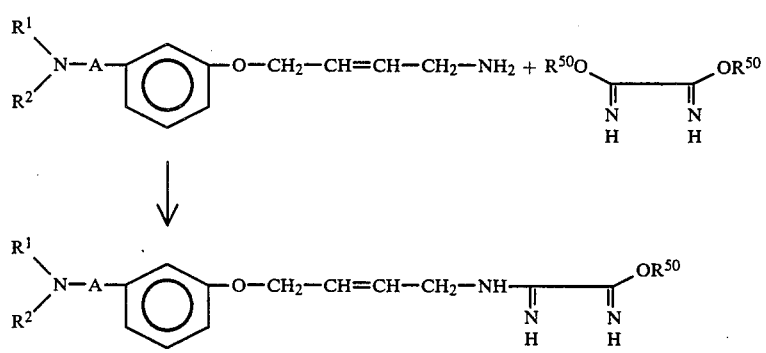

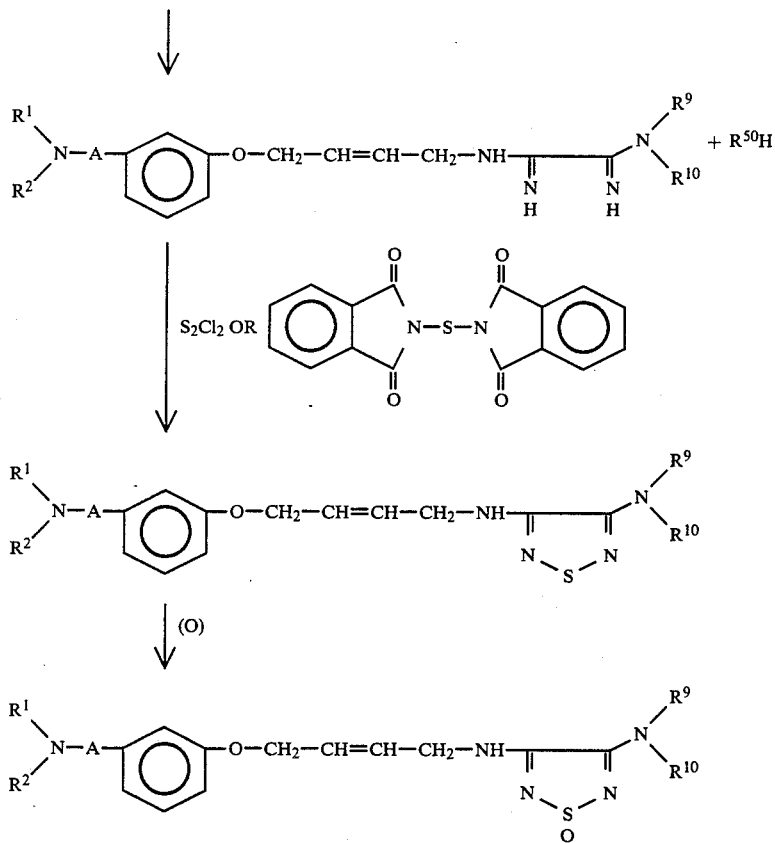
(E) Compounds wherein Z is a group represented by:
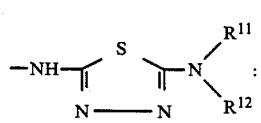:
Such a compound can be prepared through the following reactions:
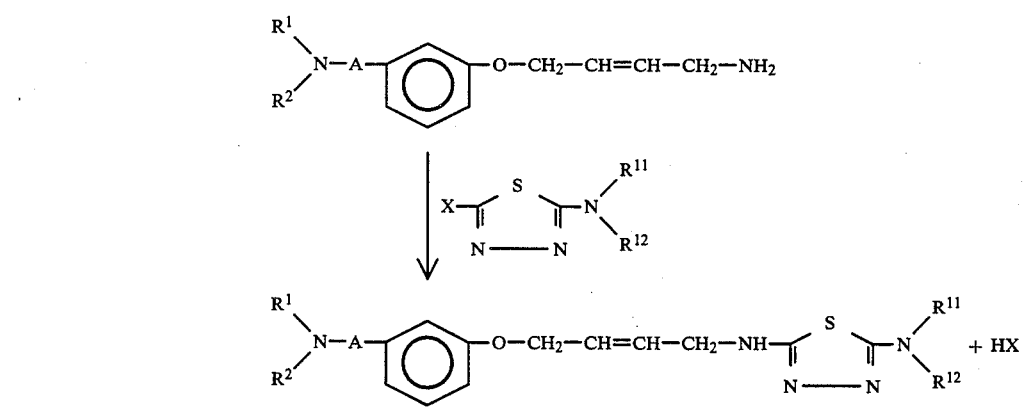
Alternatively, such a compound may be prepared by the process including the following first and second steps:
First Step:
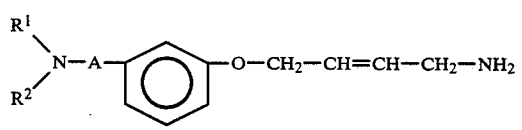

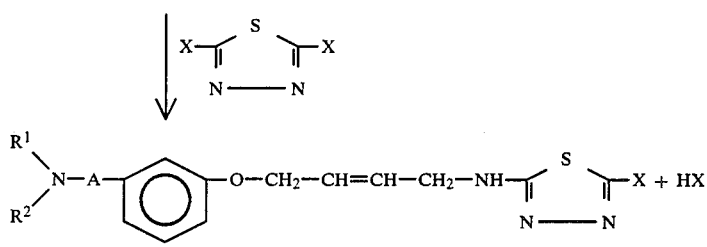

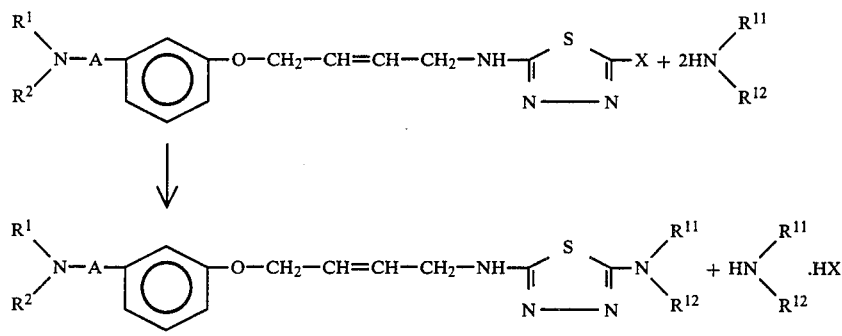

Second Step:

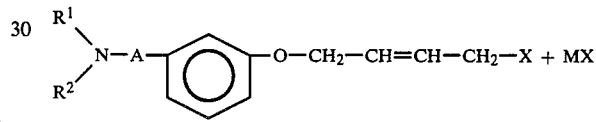

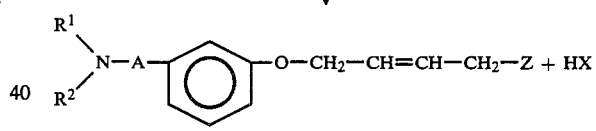

wherein $R^1$, $R^2$, A, $R^{11}$, $R^{12}$ and X are the same as defined above.

Although the latter process has a larger number of steps, it is generally favoured because of decreased by-products and increased yield.

As further modified processes for the preparation of the compounds represented by the general formula (I), it may be mentioned that utilizing the following reaction:

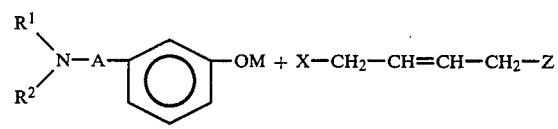

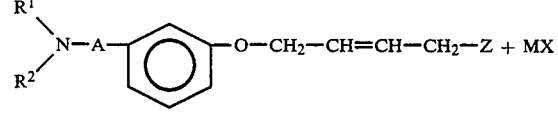

wherein $R^1$, $R^2$, A, and Z are the same as defined above; M is an alkali metal, preferably sodium or potassium; and X is a halogen atom, such as chlorine, bromine or iodine; and that utilizing the following reaction:

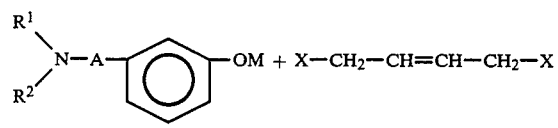

wherein $R^1$, $R^2$, A, X, M and Z are the same as defined above.

Pharmaceutical Efficacies of the Compounds of the Invention

Some compounds of this invention were tested and compared with Cimetidine which has been widely used for clinic applications as a medicine for digestive ulcers as having an antagonistic function on the histamine $H_2$-receptor.

(A) Inhibition Effect on Gastric Acid Secretion Induced by Histamine in its Pylorus Ligated Rat The test was conducted by an improved method of that reported by Watanabe et al., in "Pharmacometrics", Vol. 3, No. (1), pages 7 to 14 (1969).

A male Wistar rat having a body weight of about 160 g and which had not fed for 24 hours was anesthetized by an intraperitonea dose of 1.2 g/kg of uretane. After ligating of pylorus and esophagus, the gaster anterior was incised and fitted with a double polyethylene cannula. The wall of the stomach was rinsed with 5 ml of saline at 30 minute intervals, and the quantities of gastric acid contained in each rinsing solution were measured by titration.

The basal acid secretion was initially measured three times, and then 0.2 mg/kg or 0.5 mg/kg of each of the compounds of this invention was administered subcutaneously and 3 mg/kg of histamine was administered subcutaneously after the lapse of an additional 30 minutes.

The quantity of gastric acid secreated after the operation was measured continuously for 3 hours. Within that measurement interval, three time points at which the increase in acid secretion reached a maximum level were selected, and the average quantity of gastric acid secreted at those time points was taken as the increase in acid secretion, which was compared with the increase in acid secretion of the control group to calculate the percent inhibition for secretion of gastric acid.

Percent Inhibition of Gastric Acid Secretion =

$$\left\{1 - \frac{\text{Increase in Gastric Acid Secretion of Test Group}}{\text{Increase in Gastric Acid Secretion of Control Group}}\right\} \times 100$$

(The result was shown as the average value of five runs.)

Each of the compounds having strong inhibition effects on the secretion of gastric acid was administered to each rat intraduodenally 30 minutes before the subcutaneous injection of histamine to find the amount to administer for suppressing gastric acid secretion by 50% ($ED_{50}$). The results are shown in table 1.

(B) Determination of Inhibitory Effect on Histamine $H_2$-Receptor in isolated Guinea Pig Atria A male Hartley guinea pig having a body weight of about 400 g was killed by cervical dislocation, and the artrium thereof was isolated and was suspended in an organ bath containing 50 ml of a modified Ringer solution and subjected to a tension of 1 g. The number of heart beats under such condition was recorded using a polygraph.

Initially, from $1 \times 10^{-7}$ mol to $3 \times 10^{-4}$ mol of histamine was allowed to act accumulatively to depict the curve of the dosage-reaction relationship. Likewise, the curve of the dosage of histamine-reaction relationship was depicted in the presence of $5 \times 10^{-7}$ mol to $1 \times 10^{-6}$ mol of the test sample which was injected 3 minutes before. The negative logarithm ($pA_2$) of the molar concentration of the test sample required for moving the curve obtained by single administration of histamine parallel to the right side by a two-times concentration was calculated.

The results are shown in Table 1.

(C) Acute Toxicity Test

Male ddy mice each having a body weight of about 22 g and which had not eaten for 8 hours were orally dosed with the test samples, and the general symptoms and fatalities were observed from the time immediately following the administration to 14 days after the administration.

The median lethal dose ($LD_{50}$) was calculated in accordance with the Litchfield and Wilcoxon Method.

The results are shown in Table 3.

TABLE 1

Inhibitory Effect on Gastric Acid Secretion by Histamine in Pylorus ligated rat and Determination of Inhibitory Effect on Histamine $H_2$-Receptor in isolated Guinea Pig Atria

| Sample | Secretion of Gastric Acid in Rat | | Antagonistic Action against Histamine |
|---|---|---|---|
| | Dosage mg/kg (SC) | Inhibition Rate (%) | $H_2$-Receptor ($pA_2$) Determined by Using Atrium isolated from Guinea Pig |
| Compound of Ex. 2 | 0.5 | 98** | 7.20 |
| Compound of Ex. 3 | 0.5 | 79** | 6.51 |
| Compound of Ex. 4 | 0.2 | 66 | 6.11 |
| Compound of Ex. 6 | 0.2 | 25 | 6.75 |
| Compound of Ex. 7 | 0.2 | 28 | 6.29 |
| Compound of Ex. 8 | 0.2 | 88* | 6.82 |
| Compound of Ex. 9 | 0.5 | 96** | 6.73 |
| Compound of Ex. 10 | 0.5 | 103** | 6.66 |
| Compound of Ex. 11 | 0.2 | 88** | 6.18 |
| Compound of Ex. 12 | 0.2 | 44** | 5.82 |
| Compound of Ex. 13 | 0.5 | 91** | 7.08 |
| Compound of Ex. 14 | 0.2 | −9 | 5.15 |
| Compound of Ex. 15 | 0.5 | 98** | 6.36 |
| Compound of Ex. 16 | 0.5 | 98** | 5.62 |
| Compound of Ex. 17 | 0.2 | 86* | 7.01 |
| Compound of Ex. 19 | 0.2 | 82* | 5.62 |
| Compound of Ex. 20 | 0.2 | 88** | 6.41 |
| Compound of Ex. 21 | 0.2 | 99** | 6.64 |
| Compound of Ex. 22 | 0.2 | 88** | 6.50 |
| Compound of Ex. 25 | 0.2 | 77** | 6.69 |
| Compound of Ex. 26 | 0.2 | 45* | 5.02 |
| Compound of Ex. 27 | 0.2 | 87* | 6.31 |
| Compound of Ex. 28 | 0.2 | 75 | 5.33 |
| Compound of Ex. 29 | 0.2 | 36 | 6.50 |
| Compound of Ex. 30 | 0.2 | 17 | 6.26 |
| Control (Cimetidine) | 0.5 | 41** | 6.45 |

Note:
Values affixed with * or ** indicates that significant differences as of $p < 0.05$ or $p < 0.01$ were observed as compared to the control group.

TABLE 2

Inhibitory Effect of intraduodenally administered compounds of the invention on Gastric Acid Secretion induced by Histamine in Rat

| Sample | Median effective dose ($ED_{50}$) induced Gastric Acid Section | | Efficacy Ratio relative to Cimetidine (Cimetidine = 1) |
|---|---|---|---|
| | (mg/kg) | (95% Reliability Limit) | |
| Compound of Ex. 2 | 0.046 | (0.009~0.25) | 156.5 |
| Compound of Ex. 3 | 0.036 | (0.005~0.25) | 200.0 |
| Compound of Ex. 8 | 0.070 | (0.14~3.85) | 10.3 |
| Compound of Ex. 10 | 8.0 | (not obtainable) | 0.9 |
| Compound of Ex. 11 | 0.44 | (0.07~2.62) | 16.4 |
| Compound of Ex. 13 | 0.52 | (not obtainable) | 13.8 |
| Compound of Ex. 15 | 0.066 | (0.002~1.84) | 109.1 |
| Compound of Ex. 16 | 0.04 | (0.005~0.34) | 180.0 |
| Compound of Ex. 17 | 0.82 | (0.24~2.83) | 8.8 |
| Compound of Ex. 19 | 0.88 | (not obtainable) | 8.2 |
| Compound of Ex. 20 | 0.58 | (0.34~0.99) | 9.0 |
| Compound of Ex. 21 | 2.0 | (0.39~10.2) | 3.6 |
| Compound of Ex. 22 | 0.62 | (0.18~2.11) | 11.6 |
| Compound of Ex. 27 | 0.45 | (0.16~1.26) | 16.0 |
| Compound of Ex. 28 | 0.62 | (0.18~1.54) | 11.6 |

TABLE 2-continued

Inhibitory Effect of intraduodenally administered compounds of the invention on Gastric Acid Secretion induced by Histamine in Rat

| Sample | Median effective dose ($ED_{50}$) induced Gastric Acid Section (mg/kg) | (95% Reliability Limit) | Efficacy Ratio relative to Cimetidine (Cimetidine = 1) |
|---|---|---|---|
| Reference Ex. 1 | 0.2 | (0.04~0.93) | 36.0 |
| Reference Ex. 2 | 0.44 | (0.05~3.96) | 16.4 |
| Control (Cimetidine) | 7.2 | (1.8~28.1) | 1 |

TABLE 3

Acute Toxicity Test on Mice Dosed Orally

| Sample | Median lethal dose ($LD_{50}$) mg/kg P.O. |
|---|---|
| Compound of Ex. 2 | >1500 |
| Compound of Ex. 3 | >1500 |
| Compound of Ex. 9 | 1200 |
| Compound of Ex. 10 | >1500 |
| Compound of Ex. 13 | >1500 |
| Compound of Ex. 16 | >1500 |
| Control (Cimetidine) | 3300 |

As will be clearly seen from Table 1, the inhibitive actions of the respective compounds, prepared by Examples of the invention and administered subcutaneously on gastric acid secretion induced by histamine were greater compared to that of Cimetidine. The antagonistic actions against Histamine $H_2$-receptor of the compounds of this invention were comparable with or superior to that of Cimetidine, when tested using isolated right stria of guinea pigs.

Another characteristic effecr of the compound of this invention that was ascertained is that the inhibitory effect on gastric acid secretion by the intraduodenal administration, which is similar to oral administration, was extremely higher. For instance, as shown in Table 2, from the $ED_{50}$ values of the compounds prepared, respectively, by Examples 2, 3, 15 and 16 were about 157, 200, 110 and 180 times as more effective as the $ED_{50}$ value of Cimetidine. Particularly, the compounds of this invention, prepared by Examples 15 and 16, showed activity ratio of 110 times and 180 times as high as that of Cimetidine, and the activities as such were clearly higher than those of the affinitive compounds prepared by Reference Examples 1 and 2 to show, respectively, 36 times and 16 times higher activities. (In this connection, reference should be made to Table 2.)

The acute toxicity tests conducted by administering the compounds to mice orally revealed that almost all of the tested compounds had the $LD_{50}$ values of more than 1500 mg/kg, showing that the toxicities thereof were low.

Accordingly, it should be appreciated that the compounds of this invention have remarkable utility when used as anti-pectic ulcer drugs, since they exhibit powerful inhibitory effects against Histamine $H_2$-receptor and potent suppression effects on gastric acid secretion and yet are less toxic.

Examples Of The Invention

EXAMPLE 1:

Preparation of 1-methoxy-2-[4-<3-(1-piperidinomethyl)phenoxy>-cis-2-butenylamino]-1-cyclobuten-3,4-dione One gram (0.00344 mol) of 4-<3-(1-piperidinomethyl)phenoxy>-cis-2-butenylamine was dissolved in 25 ml of absolute ethanol, and added with 0.55 g (0.00387 mol) of dimethyl squalate (prepared by the process reported by Sidney Cohen et al, in J. Amer. Chem. Soc., Vol. 88, 1533 (1966)) followed by agitation at the room temperature for 4 hours. The solvent was distilled off after the completion of the reaction, and the residue was passed through a silica gel column chromatogram to be purified, followed by elution with a mixed solution of ethyl acetate/methanol=4/1. As a result, 1.15 g (Yield: 81.0%) of the captioned compound was obtained as a light yellow oily product.

IR (neat, $cm^{-1}$): 2950, 1805, 1718, 1610, 1280, 1120, 1020, 1000, 870, 750, 700, 660.

NMR($CDCl_3$, ppm): 1.2–1.9(6H, m), 2.1–6(4H, m), 3.35(3H, s), 3.40(2H, s), 4.3–4.5(2H, m), 5.5–5.7(2H, m), 6.5–7.3(4H, m), 7.9(1H, b Disappeared by $D_2O$ treatment).

EXAMPLE 2

Preparation of 1-amino-2-[4-<3-(1-piperidinomethyl)phenoxy>-cis-2-butenylamino]-cyclobuten-3,4-dione 1.15 grams (0.0031 mol) of the 1-methoxy-2-[4-<3-(1-piperidinomethyl)phenoxy>-cis-2-butenylamine]-1-cyclobuten-3,4-dione was dissolved in 23 ml of absolute ethanol to obtain a solution through which dry ammonia gas was passed at room temperature for 20 minutes, and then the solution was agitated at room temperature for additional 2 hours. The solvent was distilled off under reduced pressure after the completion of the reaction, and the residue was passed through a silica gel column chromatogram to purify the same, followed by elution with a mixed solution of ethyl acetate/methanol=4/1. Whereupon, 0.87 g (Yield: 78.9%) of the captioned compound was obtained in a colorless crystal form, which had a melting point of 223° to 225° C.

IR(KBr, $cm^{-1}$): 3340, 3150, 2950, 1815, 1650, 1570, 1540, 1450, 1260, 1150, 1040, 780, 700, 600.

NMR(DMSO-$d_6$, ppm): 1.1–1.8(6H, m), 2.0–2.2(4H, m) 3.35(2H, s), 3.9–4.4(3H, m, Disappeared by $D_2O$ treatment), 4.5–4.7(2H, d), 5.5–5.9(2H, m), 6.5–7.2(4H, m), 7.2–7.6(2H, m, Disappeared by $D_2O$ treatment).

EXAMPLE 3

Preparation of 1-methylamino-2-[4-<3-(1-piperidinomethyl)-phenoxy>-cis-2-butenylamino]-cyclobuten-3,4-dione 1.28 (0.00346 mol) of the 1-methoxy-2-[4-<3-(1-piperidinomethyl)phenoxy>-cis-2-butenylamino]-1-cyclobuten-3,4-dione obtained in Example 1 was dissolved in 12.8 ml of methanol, added with 10 ml of a 40% methylamine solution in methanol, and agitated at room temperature for 2 hours. The solvent was distilled off under reduced pressure after the completion of the reaction, and the residue was passed through a silica gel column chromatogram to purify the same, followed by elution with a mixed solution of ethyl acetate/methanol=4/1. Whereupon, 1.08 g (Yield: 84.6) of the captioned compound was obtained in a colorless crystal form, which had a melting point of 214° to 217° C. (decomposed at that temperature).

IR(KBr, cm⁻¹): 3190, 2950, 1805, 1665, 1570, 1400, 1280, 1040, 775, 685, 600.

NMR(DMSO-d$_6$, ppm): 1.1–1.6 (6H, m), 2.0–2.5 (4H, m), 2.95 (3H, s), 3.2 (2H, s), 4.0–4.5 (2H, m), 4.35–4.7 (2H, m), 5.4–5.7 (2H, m), 6.5–7.5 (4H, m).

EXAMPLE 4

Preparation of 1-(2-propagylamino)-2-[4-<3-(1-piperidinomethyl)-phenoxy>-cis-2-butenylamino]-1-cyclobuten-3,4-dione

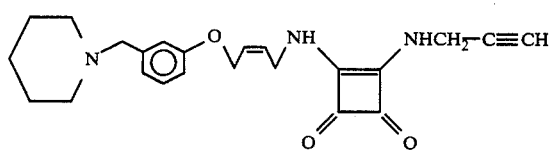

Yield: 69.9%

Melting Point: 114° to 119° C.

IR(KBr, cm⁻¹): 3300, 2950, 1620, 1490, 1450, 1340, 1260, 1030.

NMR(CDCl$_3$, ppm): 1.1–1.6 (6H, m), 2.1–2.7 (4H, m), 3.5 (2H, s), 4.0–4.3 (2H, m), 4.3–4.8 (2H, m), 5.4–6.0 (2H, m), 6.5–7.5 (4H, m).

EXAMPLE 5

Preparation of 1-methoxy-2-[4-<3-(1-piperidinomethyl)phenoxy>-trans-2-butenylamino]-1-cyclobuten-3,4-dione

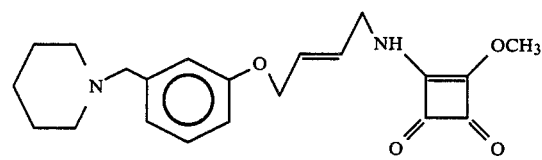

Light Yellow Oily Product

Yield: 74.0%

IR(neat, cm⁻¹): 3210, 2950, 1810, 1720, 1610, 1380, 1350, 1260, 1160, 1040, 800.

NMR(CDCl$_3$, ppm): 1.2–1.7 (6H, m), 2.1–2.5 (4H, m), 3.4 (2H, s), 3.8–4.2 (2H, m), 4.3 (3H, s), 4.3–4.6 (2H, m), 5.7–5.95 (2H, m), 6.5–7.3 (4H, m).

EXAMPLE 6

Preparation of 1-amino-2-[4-<3-(1-piperidinomethyl)phenoxy>-trans-2-butenylamino]-1-cyclobuten-3,4-dione

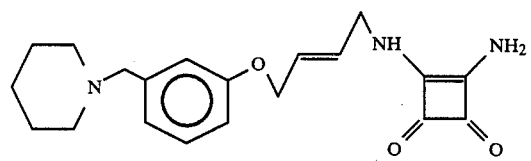

Yield: 82%

Melting point: 220° to 227° C.

IR(KBr, cm⁻¹): 3320, 3150, 2950, 1810, 1650, 1570, 1340, 1260, 1150, 960, 860, 770, 690.

NMR(DMSO-d$_6$/CDCl$_3$, ppm): 1.2–1.9 (6H, m), 2.1–2.6 (4H, m), 3.35 (2H, s), 4.0–4.3 (2H, m), 4.35–4.6 (2H, m), 5.7–6.0 (2H, m), 6.5–7.2 (4H, m), 7.15–7.3 (2H, m Disappeared by D$_2$O treatment).

EXAMPLE 7

Preparation of 1-methylamino-2-[4-<3-(1-piperidinomethyl)-phenoxy>-trans-2-butenylamino]-1-cyclobuten-3,4-dione

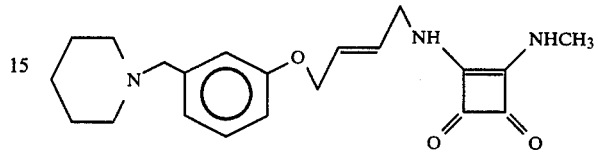

Yield: 77.2%

Melting point: 216° to 218° C.

IR(KBr, cm⁻¹): 3200, 2950, 1810, 1660, 1570, 1390, 1260, 1150, 1020.

NMR(DMSO-d$_6$/CDCl$_3$, ppm): 1.0–1.7 (6H, m), 1.9–2.6 (4H, m), 3.1 (3H, s), 3.3 (2H, s), 3.9–4.3 (2H, m), 4.3–4.6 (2H, m), 5.6–6.0 (2H, m), 6.5–7.3 (4H, m), 8.1 (1H, bro., Disappeared by D$_2$O treatment).

EXAMPLE 8

Preparation of 1-amino-2-[4-<3-(1-pyrrolidinomethyl)phenoxy>-cis-2-butenylamino]-1-cyclobuten-3,4-dione

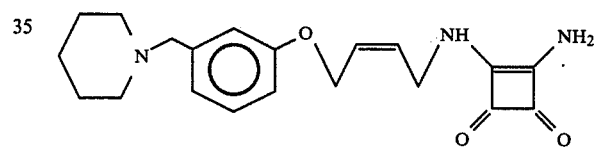

Yield: 68.5%

Melting Point: 212° to 217° C.

IR(KBr, cm⁻¹): 3150, 2970, 2800, 1810, 1650, 1570, 1535, 1330, 1270, 1150, 1080, 690.

NMR(DMSO-d$_6$, ppm): 1.4–1.9 (4H, m), 2.2–2.6 (4H, m) 3.45 (2H, m), 3.6–4.0 (2H, bro. Vanished by the treatment with D$_2$O), 4.0–4.8 (2H, m), 4.45–4.7 (2H, m), 5.5–5.7 (2H, m), 6.5–7.1 (4H, m).

EXAMPLE 9

Preparation of 6-amino-5-[4-<3-(1-piperidinomethyl)phenoxy>-cis-2-butenylamino]-1,2,4-triazin-3-one 1.2 g (0.0046 mol) of 4-<3-(1-pyperidinomethyl)-phenoxy>-cis-2-butenylamine and 0.6 g (0.0046 mol) of 6-amino-5-mercapto-1,2,4-triazin-3-one (prepared by the process reported by C. C. Tzeng et al, J. Org. Chem., Vol. 48, 1273 (1983)) were refluxed in 30 ml of methanol for an hour. The solvent was distilled off after the completion of the reaction, and the residue was added with a small quantity of methanol and then cooled. The precipitated crystal was recrystallized from ethanol to obtain 1.3 g (Yield: 76.0%) of a colorless crystal. The melting point of the thus obtained crystal was 212° to 214° C. at which the crystal was decomposed.

IR(KBr, cm⁻¹): 3250, 2950, 1640, 1460, 1260, 1040.

NMR(DMSO-d$_6$, ppm): 1.2–1.8 (6H, m), 2.0–2.5 (4H, m), 3.33 (2H, s), 3.8–4.3 (2H, m), 4.62 (2H, d), 5.49 (2H, m) 5.3–5.9 (2H, m), 6.5–7.3 (4H, m), 7.82 (1H, bro. Disappeared by D$_2$O treatment), 11.46 (1H, bro., Disappeared by D$_2$O treatment).

EXAMPLE 10

Preparation of 6-methylamino-5-[4-<3-(1-piperidinomethyl)-phenoxy>-cis-2-butenylamino]-1,2,4-triazin-3-one

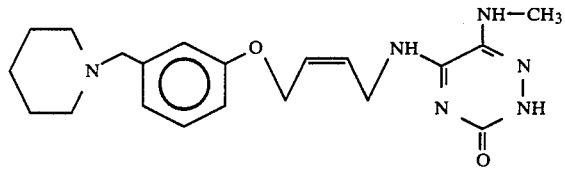

Yield: 74%
Melting Point: 73° to 75° C.
IR(KBr, cm$^{-1}$): 3350, 2950, 1500, 1430, 1280, 1050, 790.
NMR(DMSO-d$_6$, ppm): 1.1–1.8 (6H, m), 2.1–2.5 (4H, m), 2.69 (3H, d), 3.33 (2H, s), 3.8–4.3 (2H, m), 4.60 (2H, d), 5.2–6.1 (2H, m), 5.95 (1H, bro. Disappeaved by D$_2$O treatment) 6.4–7.3 (4H, m).

EXAMPLE 11

Preparation of 6-amino-5-[4-<3-(1-piperidinomethyl)phenoxy>-trans-2-butenylamino]-1,2,4-triazin-3-one

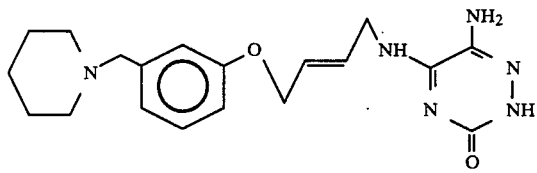

Yield: 45.7%
Melting Point: 215° to 222° C.
IR(KBr, cm$^{-1}$): 3220, 2940, 1640, 1580, 1470, 1340, 1300, 1255, 1155, 1035, 770, 690.
NMR(DMSO-d$_6$/CDCl$_3$, ppm): 1.2–1.8 (6H, m), 1.95–2.55 (4H, m), 3.3 (2H, s), 3.8–4.2 (2H, m), 4.2–4.55 (2H, m), 5.3–6.0 (4H, m), 6.4–7.2 (4H, m) 7.7–8.1 (1H, bro, Disappeared by D$_2$O treatment).

EXAMPLE 12

Preparation of 2-methyl-6-methylamino-5-[4-<3-(1-piperidinomethyl)phenoxy>-trans-2-butenylamino]-1,2,4-triazin-3-one

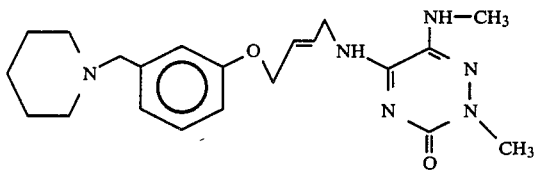

Yield: 52.8%
Melting Point: 139° to 140° C.
IR(KBr, cm$^{-1}$): 3300, 2940, 1590, 1520, 1440, 1360, 1260, 1160, 1020, 965, 860, 800, 770, 700, 600, 550, 480.

NMR(CDCl$_3$, ppm): 1.25–1.8 (6H, m), 2.15–2.5 (4H, m) 2.8 (3H, s), 3.35 (2H, s), 3.5 (3H, s), 3.9–4.2 (2H, m), 4.2–4.5 (2H, m), 5.65–5.95 (2H, m), 6.4–7.25 (4H, m), 8.2–8.75 (1H, bro. Disappeared by D$_2$O treatment).

EXAMPLE 13

Preparation of 4-amino-6-[4-<3-(1-piperidinomethyl)phenoxy>-cis-2-butenylamino]-(1H)-pyrimidin-2-one One gram (0.0038 mol) of 4-<3-(1-piperidinomethyl)phenoxy>-2-butenylamine and 0.23 g (0.0013 mol) of 6-amino-4-chloro-(1H)-pyrimidin-2-one hydrochloride (prepared by the process reported by Wolfgang Pfleiderene et al, Ann., 657, 149 (1962)) were refluxed under heating with 1.5 ml of water for 50 minutes. After the completion of the reaction, the precipitated crystal was filtered and dried, and then recrystallized from methanol to obtain 0.38% (Yield: 81.3%) of the captioned compound. The thus obtained crystalline product had a melting point of 225° to 227° C.

IR(KBr, cm$^{-1}$): 3500, 3170, 2950, 1680, 1650, 1620, 1545, 1525, 1450.
NMR(DMSO-d$_6$, ppm): 1.2–1.6 (6H, m), 2.1–2.4 (4H, m), 2.3 (2H, s), 3.6–4.0 (2H, m), 4.45–4.7 (2H, m), 4.65 (1H, s), 5.45–5.7 (2H, m), 6.5–7.1 (8H, m, 4H Disappeaved by D$_2$O treatment).

EXAMPLE 14

Preparation of 1-methyl-4-amino-6-[4-<4-<3-(1-piperidinomethyl)phenoxy>-trans-2-butenylamino]-(1H)-pyrimidin-2-one

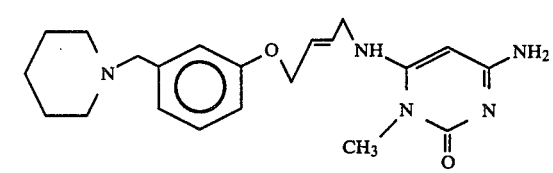

Yield: 72.6%
Melting Point: 169° to 175° C.
IR(KBr, cm$^{-1}$): 3450, 3200, 2940, 2800, 1640, 1620, 1570, 1490, 1365, 1270, 1040, 970, 860, 780, 690, 640.

EXAMPLE 15

Preparation of 3-amino-4-[4-<3-(1-piperidinomethyl)phenoxy>-cis-2-butenylamino]-1,2,5-thiadiazol-1-oxide 1.3 g (0.005 mol) of 4-4-<3-(1-piperidinomethyl)phenoxy>-cis-2-butenylamine was dissolved in 25 ml of absolute alcohol and added with 0.81 g (0.005 mol) of 3,4-dimethoxy-1,2,5-thiadiazol-1-oxide (prepared by the process disclosed by Japanese Patent Laid-open publication No. 40675/1981), followed by agitation at room temperature for an hour. Thereafter, dry ammonia gas was passed through the solution for 20 minutes, and the solution was agitated for additional one hour to complete the reaction.

The solvent was distilled off under reduced pressure, and the residue was passed through a silica gel column chromatogram to purify the same, followed by elution with a mixed solution of ethyl acetate/methanol=4/1, to obtain 1.1 g of the captioned compound in a colorless crystal (Yield: 58.7%). The thus obtained product had a melting point of 134° to 137° C.

IR(KBr, cm$^{-1}$): 3310, 3150, 3050, 2950, 1620, 1260, 1160, 1040, 850, 695, 520.

NMR(CDCl$_3$, ppm): 1.2–1.9 (6H, m), 2.2–2.7 (4H, m), 2.9 (3H, s), 3.5 (2H, s), 3.8–4.2 (2H, m), 4.4–4.7 (2H, m), 5.5–5.8 (2H, m), 6.5–7.3 (4H, m).

EXAMPLE 16

Preparation of 3-methylamino-4-[4-<3-(1-piperidinomethyl)-phenoxy>-cis-2-butenylamino]-1,2,5-thiadiazol-1-oxide Generally following to the procedures as described in Example 15, except in that the reaction with ammonia gas was replaced by the reaction with 2 ml of a 40% methylamine solution in methanol, to obtain 0.89 g (Yield: 46%) of the captioned compound as a light yellow oily product.

IR(neat, cm$^{-1}$): 3300, 3150, 3050, 2950, 1620, 1260, 1160, 1040, 850, 695, 520.

NMR(CDCl$_3$, ppm): 1.2–1.9 (6H, m), 2.2–2.7 (4H, m), 2.9 (3H, s), 3.5 (2H, s), 3.8–4.2 (2H, m), 4.4–4.7 (2H, m), 5.5–5.8 (2H, m), 6.5–7.3 (4H, m).

EXAMPLE 17

Preparation of 3-amino-4-[4-<3-(1-pyrrolidinomethyl)phenoxy>-cis-2-butenylamino]-1,2,5-thiadiazol-1-oxide

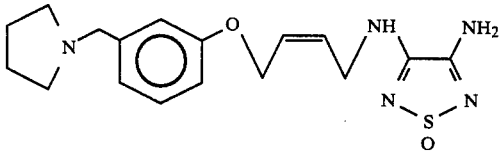

Yield: 81.0%
Melting Point: 76° to 84° C.
IR(KBr, cm$^{-1}$): 3250, 2800, 1670, 1580, 1490, 1450, 1280, 1050, 880, 810, 700, 630.

NMR(CDCl$_3$, ppm): 1.4–2.0 (4H, m), 2.2–2.7 (4H, m), 3.3–3.7 (2H, s), 3.7–4.3 (2H, m), 4.4–4.8 (2H, m), 5.4–5.9 (2H, m), 6.5–7.4 (6H, m, 2H Disappeaved by D$_2$O treatment).

EXAMPLE 18

Preparation of 3-methylamino-4-[4-<3-(1-pyrrolidinomethyl)-phenoxy>-cis-2-butenylamino]-1,2,5-thiadiazol-1-oxide

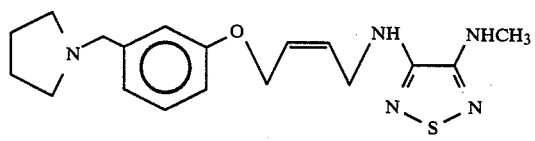

The resultant product was a light yellow oily substance, and the yield was 70.5%.

IR (nest, cm$^{-1}$): 3400, 2950, 2500, 1600, 1490, 1450, 1370, 1330, 1250, 1170, 1040, 900, 840, 780, 695, 625, 520.

NMR (DMSO-d$_6$/CDCl$_3$, ppm): 1.7–2.0 (4H, m), 2.7–3.2 (4H, m), 4.0 (2H, s), 4.2 (3H, s), 4.4–4.7 (2H, m), 5.5–5.7 (2H, m), 6.7–7.4 (4H, m).

EXAMPLE 19 preparation of 3-isopropylamino-4-[4-<3-(1-piperidinomethyl)-phenoxy>-cis-2-butenylamino]-1,2,5-thiadiazol-1-oxide

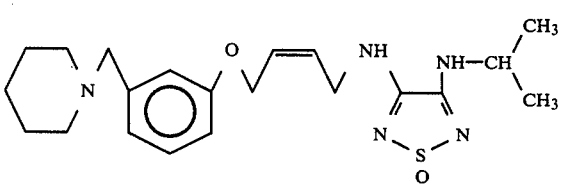

Yield: 67.3%
Melting Point: 105° to 110° C.
IR(KBr, cm$^{-1}$): 3300, 2950, 1610, 1570, 1490, 1450, 1370, 1340, 1260, 1150, 1030, 910, 875, 690, 630, 530.

NMR(CDCl$_3$, ppm): 0.9–1.5 (6H, d), 1.3–1.8 (6H, m), 2.15–2.6 (4H, m), 3.45 (2H, s), 3.75–4.35 (2H, m), 4.45–4.75 (2H, m), 5.55–5.95 (2H, m), 6.45–7.75 (4H, m), 7.65–8.45 (1H, bro, Vanished by the treatment with D$_2$O).

EXAMPLE 20

Preparation of 3-n-propylamino-4-[4-<3-(1-piperidinomethyl)-phenoxy>-cis-2-butenylamino]-1,2,5-thiadiazol-1-oxide

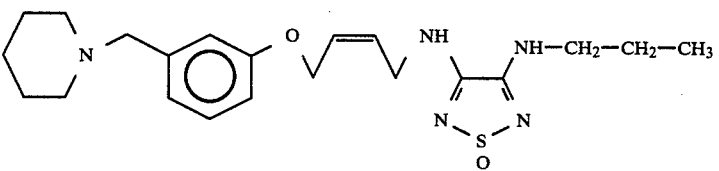

The resultant product was a light yellow oily substance, and the yield was 85.3%.

IR(neat, cm$^{-1}$): 3300, 2950, 1610, 1580, 1490, 1450, 1345, 1260, 1160, 1040, 950, 840, 775, 695.

NMR(CDCl$_3$, ppm): 0.7–1.1 (3H, t), 1.2–1.8 (6H, m), 2.15–2.6 (4H, m), 2.8–3.5 (4H, m), 3.45 (2H, s), 3.8–4.2 (2H, m), 4.4–4.7(2H, m), 5.5–5.8(2H, m), 6.5–7.1(4H, m).

EXAMPLE 21

Preparation of 3-<4-(3-dimethylaminomethylphenoxy)-cis-2-butenylamino>-4-amino-1,2,5-thiadiazol-1-oxide

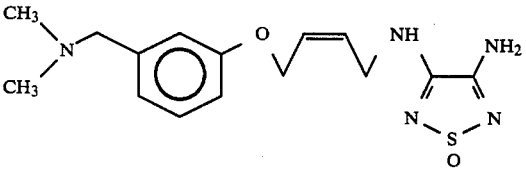

Yield: 43.5%

Melting Point: 78° to 80° C.

IR(KBr, cm$^{-1}$): 3300, 2950, 1670, 1590, 1500, 1450, 1260, 1160, 1030, 880, 810, 700, 630.

NMR(DMSO-d$_6$, ppm): 2.35 (6H, s), 3.5 (2H, s), 4.1–4.4 (2H, m), 4.6–4.9 (2H, m), 5.6–6.1 (2H, m), 6.6–7.3 (4H, m), 7.7–8.1 (2H, bro. Vanished by the treatment with D$_2$O), 8.3–8.7 (1H, bro. Disappeared by D$_2$O treatment).

EXAMPLE 22

Preparation of 3-<4-(3-dimethylaminomethylphenoxy)-cis-2-butenylamino>-4-methylamino-1,2,5-thiadiazol-1-oxide

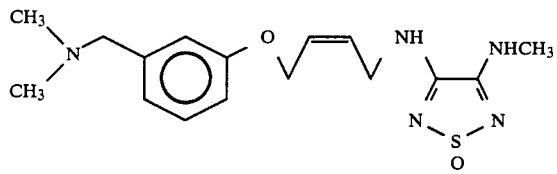

The resultant product was a light yellow oily substance, and the yield was 72.3%.

IR(neat, cm$^{-1}$): 3310, 3050, 1610, 1490, 1450, 1415, 1260, 1160, 1040, 840, 695, 630, 580, 520.

NMR(CDCl$_3$, ppm): 2.45 (6H, s), 3.1 (3H, 8), 3.65 (2H, s), 4.1–4.3 (2H, m), 4.6–4.9 (2H, m), 5.7–6.1 (2H, m), 6.7–7.4 (4H, m).

EXAMPLE 23

Preparation of 3-amino-4-[4-<3-(1-piperidinomethyl)phenoxy>-cis-2-butenylamino]-1,2,5-thiadiazol Step (A): Preparation of N-[4-<3-(1-piperidinomethyl)phenoxy>-cis-2-butenyl]-ethanediimidamide trihydrochloride;

4.2 g (0.0112 mol) of 3-amino-4-[4-<3-(1-piperidinomethyl)phenoxy>-cis-2-butenylamino]-1,2,5-thiadiazol-1-oxide obtained in Example 15 was dissolved in 100 ml of methanol, added with 7.99 ml of conc. hydrochloric acid while cooling, and then agitated at room temperature for 4 hours.

The reaction mixture was concentrated under reduced pressure after the completion of the reaction, and the residue was added with 10 ml of 2-propanol followed by concentration under reduced pressure. The aforementioned operations were repeated for additional two cycles to remove water by azeotropic boiling. The crystalline residue was added with 3 ml of absolute alcohol, and the admixture was ground intimately, cooled and then filtered to obtain 3.3 g of the captioned compound in a colorless powdered crystal form (Yield: 71.8%). The melting point of the product compound was 180° to 188° C., at which the product was decomposed.

IR(KBr, cm$^{-1}$): 2950, 1700, 1500, 1455, 1270, 1170, 1050, 980, 770, 700.

NMR(DMSO-d$_6$ppm): 1.2–2.2(6H, m), 2.2–3.8(4H, m), 4.2(2H, s), 4.5–4.9(2H, m), 5.5–6.0(2H, m), 6.7–7.5(4H, m), 9.5–11.00(4H, b).

Step (B): Preparation of 3-amino-4-[4-<3-(1-piperidinomethyl)phenoxy>-cis-2-butenylamino]-1,2,5-thiadiazol;

A mixture of 1.0 g (0.00228 mol) of N-[4-<3-(1-piperidinomethyl)phenoxy>-cis-2-butenyl]-ethanediimidamide trihydrochloride prepared by the step (A) of this Example, 10 ml of CH$_2$Cl$_2$ and 0.69 g (0.00684 mol) of triethylamine was added with 2.216 g (0.0068 mol) of N, N'-thiobisphthalimide (prepared by the process reported by M. V. Kalnins, Canadian Journal of Chem., 44, 2111 (1966)) little by little at room temperature under agitation, followed by additional agitation at room temperature for 2 hours.

After the completion of the reaction, 10 ml of a 20% aquesous KOH solution was added thereto and shaked. Then, the organic phase was separated and dried with MgSO$_4$. The solvents were distilled off under reduced pressure, and the residue was purified by passing through a silica gel column chromatogram, followed by elution with a mixed solution of ethyl acetate ethanol-/ammonia=6/1/1, whereby 0.35 g of the captioned compound was obtained as a light yellow oily product (Yield: 40.0%)

IR(neat, cm$^{-1}$): 3400, 2950, 1640, 1570, 1450, 1250, 1120, 1040, 990, 775, 700, 620.

NMR(CDCl$_3$, ppm): 1.15–1.85(6H, m), 2.1–2.6(4H, m), 3.37(2H, s), 3.7–4.3(2H, m), 4.3–4.65(2H, d), 4.5–5.2(2H, b, Disappeared by D$_2$O treatment), 5.4–6.0 (2H, m), 6.5–7.3(4H, m).

EXAMPLE 24

PREPARATION OF 3-[4-<3-(1-piperidinomethyl)phenoxy>-trans-2-butenylamino]-4-amino-1,2,5-thiadiazol

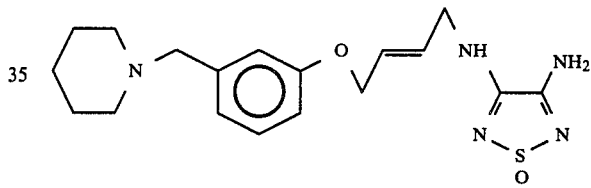

The oily product was obtained at an yield of 27.5%.

IR(neat, cm$^{-1}$): 3400, 3350, 3210, 2950, 1660, 1490, 1450, 1255, 1160, 1040, 850, 770, 690.

NMR(CDCl$_3$, ppm): 1.2–1.7(6H, m), 2.1–2.6(4H, m), 3.25(2H, s), 3.6–4.0(2H, m), 4.2–4.6(2H, m), 5.5–6.0(2H, m), 6.5–7.3(4H, m).

EXAMPLE 25

Preparation of 2-amino-5-[4-<3-(1-piperidinomethyl)phenoxy>-trans-2-butenylamino]-1,3,4-thiadiazol 0.65 g (0.0025 mol) of 4-<3-(1-piperidinomethyl)phenoxy>-trans-2-butenylamine and 0.37 g (0.0025 mol) of 2-amino-5-bromo-1,3,4-thiadiazol (prepared by the process reported by Pathgeb, Paul et al, German Offenlegeschrift No. 2,156,672) were dissolved in 10 ml of ethanol and sealed in a Bonbenrohr, and then the content in the Bonbenrohr was stirred at a temperature of from 100° to 110° C. for 8 hours.

After the completion of the reaction, the solvent was distilled off under reduced pressure, and the residue was purified by passing the same through a silica gel column chromatogram, followed by elution with a mixed solution of ethyl acetate/methanol=4/1, whereby 0.55 g of the captioned compound was obtained in a colorless crystal form (Yield: 64.0%). The melting point of the product crystal was 133° to 134° C. (in isopropanol).

IR(KBr, cm⁻¹): 3300, 2950, 1620, 1584, 1520, 1455, 1340, 1300, 1260, 1160, 1140, 1035, 960, 875, 770, 695.

NMR(CDCl₃, ppm): 1.1–1.9(6H, m), 2.1–2.7(4H, m), 3.5(2H, s), 3.65–4.0(2H, m), 4.2–4.6(2H, m), 5.2–6.1(m, 4–5H, Disappeared by D₂O treatment).

EXAMPLE 26

Preparation of 2-methylamino-5-[4-<3-(1-piperidinomethyl)-phenoxy>-trans-2-butenylamino]-1,3,4-thiadiazol Step (A): Preparation of 2-bromo-5-[4-<3-(1-piperidinomethyl)-phenoxy>-trans-2-butyenylamino]-1,3,4-thiadiazol;

0.7 g (0.002 mol) of 4-<3-(1-piperidinomethyl)-phenoxy>-trans-2-butenylamine was dissolved in 10 ml of ethanol, and added with 0.66 g (0.0027 mol) of 2,5-dibromo-1,3,4-thiadiazol (prepared by the process reported by R. Stolle and K. Fehrenbach, J. Prakt. Chem., 122, 289–318 (1927)) and the admixture was agitated under reflux for 8 hours.

After the completion of the reaction, the solvent was distilled off and the residue was purified by passing the same through a silica gel column chromatogram, followed by elution with a mixed solution of ethyl acetate/methanol=9/1, whereby 0.7 g of the captioned compound was obtained in a light yellow oily product (Yield: 61.0%).

IR(neat, cm⁻¹): 3300, 2950, 1440, 1350, 1260, 1160, 1030, 770, 700.

NMR(CDCl₃, ppm): 1.3–1.8(6H, m), 2.15–2.6(4H, m), 3.4(2H, s), 3.8–4.1(2H, m), 4.3–4.6(2H, m), 5.75–6.0(2H, m), 6.5–7.3(4H, m).

Step (B): Preparation of 2-methylamino-5-[4-<3-(1-piperidinomethyl)-phenoxy>-trans-2-butenylamino]-1,3,4-thiadiazol 0.5 g of the brominated product obtained through the step (A) set forth hereinabove was dissolved in 10 ml of a 40% solution of methylamine in methanol, and the solution was sealed in a Bonbenrohr and the content in the Bohnbenrohr was stirred at 100° C. for 3 hours.

After the completion of the reaction, the solvent was distilled off and the residue was purified by passing the same through a silica gel column chromatogram, followed by elution with a mixed solution of ethyl acetate/methanol=9/1, whereby 0.2 g of the captioned compound was obtained in a colorless crystal form (Yield: 50%). The thus obtained crystal had a melting point of 87° to 92° C.

IR(KBr, cm⁻¹): 3200, 2950, 1615, 1500, 1260

NMR(CDCl₃, ppm): 1.2–1.8(6H, m), 2.15–2.6(4H, m), 3.3(3H, s), 3.4(2H, s), 3.6–4.0(2H, m), 4.2–4.5(2H, m), 4.6–5.1(1H, b, Disappeared by D₂O treatment), 5.65–5.9(2H, m), 6.5–7.2(4H, m).

EXAMPLE 27

Preparation of 2-amino-5-[4-<3-(1-piperidinomethyl)-phenoxy>-cis-2-butenylamino]-1,3,4-thiadiazol

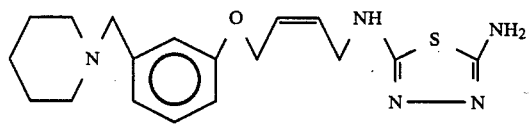

An oily product was obtained at an yield of 63.7%.

IR(neat, cm⁻¹): 3270, 3170, 2950, 1580, 1510, 1440, 1340, 1250, 1160, 1110, 1030, 990, 860, 770, 690.

NMR(CDCl₃, ppm): 1.2–1.9(6H, m), 2.2–2.6(4H, m), 3.4(2H, s), 3.8–4.2(2H, m), 4.4–4.8(2H, m), 5.5–6.02H, m), 5.1–5.6(2H, bro. Disappeaved by D₂O treatment), 6.5–7.4(5H, m, Disappeaved by D₂O treatment).

EXAMPLE 28

Preparation of 2-methylamino-5-[4-<3-(1-piperidinomethyl)-phenoxy>-cis-2-butenylamino]-1,3,4-thiadiazol

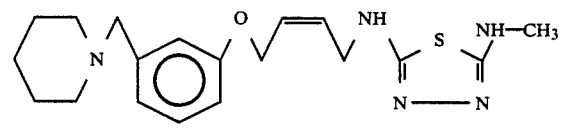

An oily product was obtained at an yield of 72.4%

IR(neat, cm⁻¹): 3210, 2950, 1610, 1490, 1440, 1330, 1255, 1145, 1035, 860, 770, 690.

NMR(CDCl₃, ppm): 1.4–1.9(6H, m), 2.3–2.7(4H, m), 3.3(3H, s), 3.5(2H, s), 3.8–4.2(2H, m), 4.4–4.8(2H, m), 5.5–5.9(2H, m), 6.6–7.5(5H, m, 1H Disappeared by D₂O treatment).

EXAMPLE 29

Preparation of 2-amino-5-[4-<3-(1-pyrrolidinomethyl)-phenoxy>-cis-2-butenylamino]-1,3,4-thadiazol

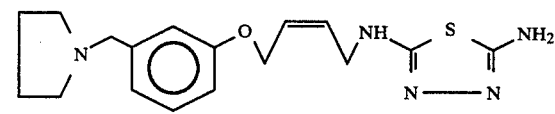

Yield: 45.8%

Melting Point: 42° to 46° C. IR(KBr, cm¹): 3250, 2950, 2700, 2450, 1600, 1580, 1510, 1450, 1260, 1160, 1020, 860, 780, 700.

NMR (CDCl₃, ppm): 1.5–2.2(4H, m), 2.8–3.5(4H, m), 4.25(2H, s), 3.5–4.0(2H, m), 4.4–4.8(2H, m), 4.6–5.1(2H, m, bro. Disappeared by D₂O treatment).

EXAMPLE 30

Preparation of 2-methylamino-5-[4-<3-(1-pyrrolidinomethyl)-phenoxy>-cis-2-butenylamino]-1,3,4-thiadiazol

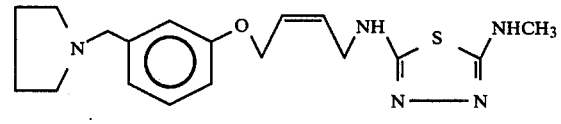

Yield: 79.0%

Melting Point: 44° to 49° C.

IR(KBr, cm⁻¹): 3230, 2950, 1610, 1490, 1450, 1380, 1330, 1260, 1030, 870, 780, 690.

NMR(DMSO-d₆/CDCl₃, ppm): 1.2–1.7(4H, m), 2.0–2.6(4H, m), 3.0(3H, s), 3.4(2H, s), 3.4–3.7(2H, m), 4.1–4.5(2H, m), 5.1–5.5(2H, m), 5.4–5.8(1H, bro. Disappeared by D₂O treatment), 6.0–7.0(4H, m).

REFERENCE EXAMPLE 1

Preparation of 3-amino-4[4-<3-(1-piperidinomethyl)phenoxy>-cis-2-butenylamino]-1,2,5-thiadiazol-1,1-dioxide The captioned was prepared by repeating similar procedures as in Example 15, except that 3,4-dimethoxy-1,2,5-thiadiazol-1,1-dioxide was used in lieu of 3,4-dimethoxy-1,2,5-thiadiazol-1-oxide.

IR(KBr, cm$^{-1}$): 3310, 2950, 1640, 1610, 1450, 1330, 1150, 870, 650, 540.

NMR(DMSO-d$_6$CDCl$_3$, ppm): 1.0–1.7(6H, m), 2.0–2.6(4H, m), 3.35(2H, s), 3.6–4.2(2H, m), 4.3–4.7(2H, m), 5.4–5.7(2H, m), 6.6–7.2(4H, m).

REFERENCE EXAMPLE 2

Preparation of 3-methylamino-4-[4-<3-(1-piperidinomethyl)-phenoxy>-cis-2-butenylamino]-1,2,5-thiadiazol-1,1-dioxide The captioned compound was prepared by repeating similar procedures as in Reference Example, 1, except that a 40% methylamine solution in methanol was used in lieu of ammonia gas.

IR(neat, cm$^{-1}$): 3350, 2900, 1630, 1450, 1270, 1150, 1030, 910, 770, 640, 540.

NMR(DMSO-d$_6$/CDCl$_3$, ppm): 1.1–1.7(6H, m), 2.0–2.6(4H, m), 2.95(3H, s), 3.4(2H, m), 3.9–4.3(2H, m), 4.4–4.8(2H, m), 5.5–6.0(2H, m), 6.6–7.4(4H, m).

What is claimed is:

1. An amino alkyl phenoxy derivative having the formula:

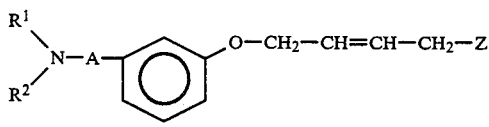

wherein $R^1$ and $R^2$ are individually hydrogen atoms or lower alkyl groups having 1 to 4 carbon atoms, or $R^1$ and $R^2$ form, together with a bonded nitrogen atom, a 4 to 8 member heterocyclic ring selected from the group consisting of azetidino-, pyrrolidino-, piperidino- and perhydroazepino- groups, which is unsubstituted or substituted by one or more hydroxyl, methoxy, ethoxy, or lower alkyl groups of 1 to 6 carbon atoms; A is a straight-chain or a branched-chain alkylene group having 1 to 4 carbon atoms; and Z is a moiety of the formula:

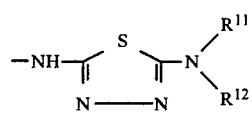

wherein $R^{11}$ and $R^{12}$ are each hydrogen, or lower alkyl, lower alkenyl, lower alkynyl or lower alkyl groups or a heterocyclic aryl alkyl group selected from the group consisting of 2-pyridinomethyl, 3-pyridinomethyl, 2-thiophenomethyl, 3-thiophenomethyl, 2-furanomethyl and 3-furanomethyl; or a heterocyclic group formed respectively by $R^{11}$ and $R^{12}$ together with the nitrogen atom bonded therewith selected from the group consisting of azetidino-, pyrrolidino- and piperidino- rings; or a hydrate, salt or solvate thereof.

2. An aminoalkylphenoxy derivative of claim 1 which is selected from the group consisting of 2-amino-5-[4-<3-(1-piperidinomethyl)phenoxy>-trans-2-butenylamino]-1,3,4-thiadiazol, 2-methylamino-5-[4-<3-(1-piperidinomethyl)-phenoxy>-trans-2-butenylamino]-1,3,4-thiadiazol, 2-amino-5-[4-<3-(1-piperidinomethyl)phenoxy>-cis-2-butenylamino]-1,3,4-thiadiazol, 2-methylamino-5-[4-<3-(1-piperidinomethyl)-phenoxy>-cis-2-butenylamino]-1,3,4thiadiaxol, 2-amino-5-[4-<3-(1-pyrrolidinomethyl)-phenoxy>-cis-2-butenylamino]-1,3,4-thadiazol and 2-methylamino-5-[4-<3-(1-pyrrolidinomethyl)-phenoxy>-cis-2-butenylamino]-1,3,4-thiadiazol.

3. An amino alkyl phenoxy derivative having the formula (I) or (II):

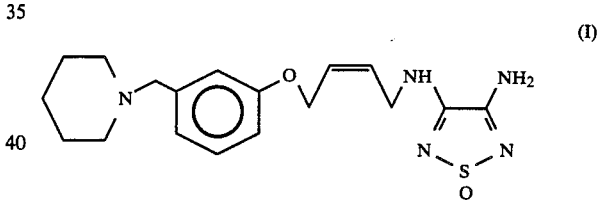

(I)

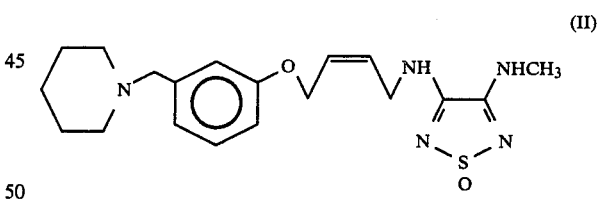

(II)

or a hydrate, salt or solvate thereof.

* * * * *